(12) United States Patent
Bertrand et al.

(10) Patent No.: US 6,303,807 B1
(45) Date of Patent: Oct. 16, 2001

(54) METAL COMPLEXES WITH A TRIDENTATE LIGAND AS POLYMERIZATION CATALYSTS

(75) Inventors: Guy Bertrand, Pechbusque; Jean-Bernard Cazaux, Aramon; Jean-Luc Faure, Toulouse, all of (FR); Hanh Nguyen, Hochiminh (VN); Régis Reau, La Chapelle des Fougeretz (FR)

(73) Assignees: Societe de Conseils de Recherches et d'Applications Scientifiques (S.C.R.A.S.); Centre National de la Recherche Scientifique (C.N.R.S.), both of (FR)

( * ) Notice: Subject to any disclaimer, the term of this patent is extended or adjusted under 35 U.S.C. 154(b) by 0 days.

(21) Appl. No.: 09/446,793
(22) PCT Filed: Jul. 6, 1998
(86) PCT No.: PCT/FR98/01433
  § 371 Date: Dec. 23, 1999
  § 102(e) Date: Dec. 23, 1999
(87) PCT Pub. No.: WO99/02536
  PCT Pub. Date: Jan. 21, 1999

(30) Foreign Application Priority Data

Jul. 8, 1997 (EP) .................................................. 97401621

(51) Int. Cl.[7] ................................ C07F 7/22; C07F 3/06; C08F 4/16
(52) U.S. Cl. .................................. 556/81; 556/9; 556/18; 556/19; 556/28; 556/81; 556/110; 556/118; 556/404; 556/424; 556/410; 526/126; 526/172; 526/266; 526/320; 502/162; 502/167
(58) Field of Search .................................. 556/9, 18, 19, 556/28, 81, 110, 118, 404, 424, 410; 526/126, 172, 320, 266; 502/162, 167

(56) References Cited

U.S. PATENT DOCUMENTS 5,344,948  9/1994  Verkade .................................. 556/51

OTHER PUBLICATIONS

XP 002048800 J. Am. Chem.Soc., 1996, 118, 5822–5823.
XP 002048801 J. Chem. Soc. Dalton Trans, 1995, Cloke et al pp. 25–30.

*Primary Examiner*—Porfirio Nazario-Gonzalez
(74) *Attorney, Agent, or Firm*—Bierman, Muserlian and Lucas

(57) ABSTRACT

The invention concerns novel compounds having the elements of group 11, 12 or 14; and a tridentate ligand, a method for preparing them and their use in particular as polymerisation catalyst.

13 Claims, 2 Drawing Sheets

METAL COMPLEXES WITH A TRIDENTATE LIGAND AS POLYMERIZATION CATALYSTS

Figure 1:
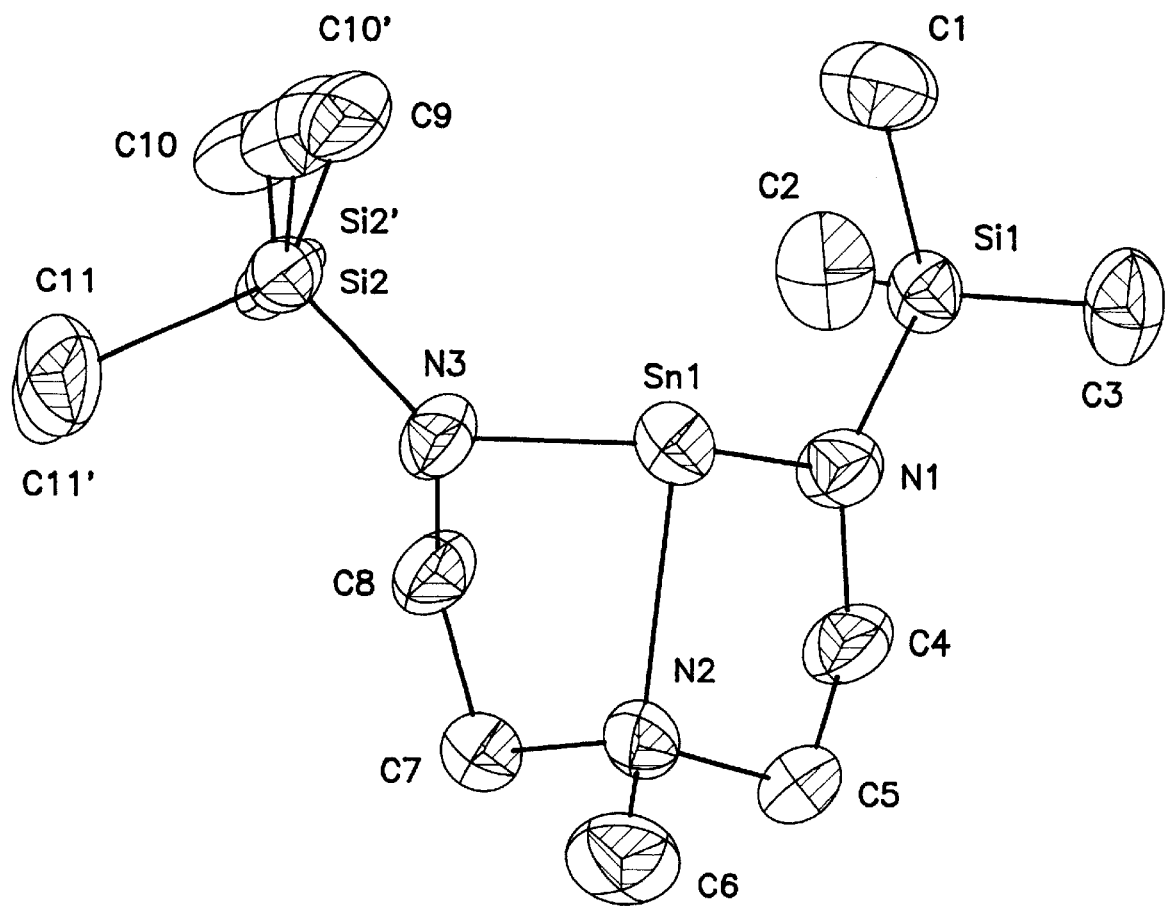

This application is a 371 of PCT/FR98/01433 filed Jul. 6, 1998.

The present invention relates to new compounds having an element of group 11, 12 or 14 and having a tridentate ligand, their preparation process and their use in particular as a polymerization catalyst.

It has been shown that each type of catalyst used for polymerizations or copolymerizations, produces respectively different polymers or copolymers in particular because of transesterification reactions which lead to the inversion of the stereogenic centres (Jedlinski et al., Macromolecules, (1990) 191, 2287 ; Munson et al., Macromolecules, (1996) 29, 8844; Montaudo et al., Macromolecules, (1996) 29, 6461). The problem is therefore to find new catalytic systems in order to obtain new polymers or copolymers, and more particularly sequenced copolymers. The use of catalytic systems allows sequenced copolymers to be obtained, allows control of the chain formation of the monomers in order to obtain specific copolymers having the appropriate properties. This is particularly useful for biocompatible copolymers the biodegradation of which is influenced by this chain formation.

Therefore a subject of the invention is the products of general formula 1

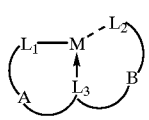

(1)

in which
- M represents an element of the groups 11, 12 or 14;
- A and B represent, independently, a carbon chain with 2 to 4 carbon atoms, optionally substituted by one of the following radicals substituted (by one or more identical or different substituents) or non substituted: alkyl, cycloalkyl or aryl, in which said substituent is a halogen atom, alkyl, nitro or cyano radical;
- $L_1$, $L_2$ and $L_3$ represent, independently, a group of formula —$E_{15}(R_{15})$— in which $E_{15}$ is an element of group 15 and
  - $R_{15}$ represents the hydrogen atom; one of the following radicals substituted (by one or more identical or different substituents) or non-substituted: cycloalkyl or aryl, in which said substituent is a halogen atom, the alkyl, nitro or cyano radical; a radical of formula RR'R"$E_{14}$— in which $E_{14}$ is an element of group 14 and R, R' and R" represent, independently, the hydrogen atom or one of the following radicals substituted (by one or more substituents identical or different) or non-substituted: alkyl, cycloalkyl, aryl, alkoxy, cycloalkoxy, aryloxy, alkylthio, cycloalkylthio or arylthio, in which said substituent is a halogen atom, the alkyl, nitro or cyano radical; or a radical of formula $SO_2R'_{15}$ in which $R'_{15}$ represents a halogen atom, an alkyl, haloalkyl or aryl radical optionally substituted by one or more substituents chosen from the alkyl, haloalkyl and halogen radicals.

In the definitions indicated above, the expression halogen represents a fluorine, chlorine, bromine or iodine atom, preferably chlorine. The expression alkyl preferably represents a linear or branched alkyl radical having 1 to 6 carbon atoms and in particular an alkyl radical having 1 to 4 carbon atoms such as methyl, ethyl, propyl, isopropyl, butyl, isobutyl, sec-butyl and tert-butyl radicals.

The term haloalkyl preferably designates the radicals in which the alkyl radical is as defined above and is substituted by one or more halogen atoms as defined above such as, for example, bromoethyl, trifluoromethyl, trifluoroethyl or also pentafluoroethyl. The alkoxy radicals can correspond to radicals in which the alkyl radical is as defined above. The methoxy, ethoxy, isopropyloxy or tert-butyloxy radicals are preferred. The alkylthio radicals preferably represent radicals in which the alkyl radical is as defined above such as, for example, methylthio or ethylthio.

The cycloalkyl radicals are chosen from the saturated or unsaturated monocyclic cycloalkyls. The saturated monocyclic cycloalkyl radicals can be chosen from radicals having 3 to 7 carbon atoms such as cyclopropyl, cyclobutyl, cyclopentyl, cyclohexyl or cycloheptyl radicals. The unsaturated cycloalkyl radicals can be chosen from cyclobutene, cyclopentene, cyclohexene, cyclopentanediene, cyclohexadiene radicals. The cycloalkoxy radicals can correspond to radicals in which the cycloalkyl radical is as defined above. The cyclopropyloxy, cyclopentyloxy or cyclohexyloxy radicals are preferred. The cycloalkylthio radicals can correspond to radicals in which the cycloalkyl radical is as defined above such as for example cyclohexylthio.

The aryl radicals can be of mono or polycyclic type. The monocyclic aryl radicals can be chosen from phenyl radicals optionally substituted by one or more alkyl radicals, such as tolyl, xylyl, mesityl, cumenyl. The polycyclic aryl radicals can be chosen from the naphthyl, anthryl, phenanthryl radicals. The aryloxy radicals can correspond to radicals in which the aryl radical is as defined above. Phenoxy, 2,4,6-tritertiobutylphenoxy, tolyloxy or mesityloxy radicals are preferred. Arylthio radicals preferably designate radicals in which the aryl radical is as defined above such as for example phenylthio.

The compounds of formula I can be presented in monomer or dimer form and more particularly, the compounds of formula I in which M represents a zinc atom are generally in dimer form.

More particularly a subject of the invention is the products of general formula 1 as defined above, characterized in that
- M represents a tin or zinc atom;
- A and B represent, independently, a carbon chain with 2 to 4 carbon atoms, and in particular a carbon chain with 2 carbon atoms;
- $L_1$, $L_2$ and $L_3$ represent, independently, a radical of formula —$E_{15}(R_{15})$— in which $E_{15}$ is a nitrogen or phosphorus atom and $R_{15}$ represents a radical of formula RR'R"$E_{14}$— in which $E_{14}$ represents a carbon or silicon atom and R, R' and R" represent, independently, the hydrogen atom or an alkyl or aryl radical and preferably the hydrogen atom or an alkyl radical.

Preferably, M represents a tin or zinc atom; A and B represent, independently, a carbon chain with 2 carbon atoms; $L_1$, $L_2$ and $L_3$ represent, independently, a radical of formula —$E_{15}(R_{15})$— in which $E_{15}$ is a nitrogen atom and $R_{15}$ represents a radical of formula RR'R"$E_{14}$— in which $E_{14}$ represents a carbon or silicon atom and R, R' and R" represent, independently, the hydrogen atom or a methyl, ethyl, propyl or isopropyl radical.

More particularly, a subject of the invention is the products described hereafter in the examples, in particular the products corresponding to the following formulae:

—[(Me₂CHNCH₂CH₂)₂NMe]Sn;

—[(Me₃SiNCH₂CH₂)₂NMe]Sn;

—[(Me₃SiNCH₂CH₂)₂NMe]Zn.

A subject of the invention is also a process for the preparation of the products of general formula 1 as defined above, characterized in that a product of formula I $$(L_1-A-L_3-B-L_2)^{2-}, 2Y+ \quad (I)$$

in which $L_1$, A, $L_3$, B and $L_2$ have the meanings indicated above and Y represents an organometallic group, a metal or the hydrogen atom, is reacted with a product of formula II $$MZ_1Z_2 \quad (II)$$

in which M has the meaning indicated above and $Z_1$ and $Z_2$ represent, independently, a parting group, in order to obtain a product of formula 1 as defined above.

The compound of formula I can also be written in the following non-ionic form $Y-L_1-A-L_3-B-L_2-Y$ (I'). When Y represents the hydrogen atom, the products of formula (I) are generally in form I'.

The reaction of a compound of general formula I with a compound of general formula II in order to obtain a compound of general formula 1, can be carried out under an inert atmosphere such as under a freon or argon atmosphere, in an aprotic solvent, at a temperature between −90 and +50° C. The compounds 1 thus obtained are purified by standard purification methods.

As aprotic solvent, aromatic hydrocarbons such as benzene, toluene; aliphatic hydrocarbons such as pentane, heptane, hexane, cyclohexane; ethers such as diethylether, dioxan, tetrahydrofuran, ethyltertiobutyl ether, chlorinated solvents such as dichloromethane or chloroform can be used.

In compounds I, Y represents an organometallic group, a metal or the hydrogen atom. The organometallic group can be a compound of formula $R'''M_1$ or $R'''_3M_2$ in which R''' represents an alkyl, cycloalkyl, aryl, alkoxy, cycloalkoxy or aryloxy radical as defined previously, $M_1$ is a zinc or mercury atom and $M_2$ a tin or lead atom; preferably, the organometallic group is chosen from the groups ZnMe, SnMe₃, SnBu₃ or PbMe₃. The metal can be an alkali metal chosen from lithium, sodium or potassium, or an alkaline-earth metal such as magnesium.

In compounds II, $Z_1$ and $Z_2$ represent, independently a parting group such as a halogen atom, an alkyl, cycloalkyl, alkoxy, aryl or aryloxy group defined as previously, or also methanesulphonyloxy, benzenesulphonyloxy, p-toluenesulphonyloxy.

The starting products of formula I are known products or can be prepared from known products. For their synthesis, the following references can be mentioned: Cloke et al., J. Chem. Soc., Dalton Trans. (1995) 25; Wilkinson and Stone, Comprehensive Organometallic Chemistry (1982) vol. 1, 557.

The products of formula II are commercial or can be manufactured by methods known to a person skilled in the art.

A subject of the invention is also the use of the products of formula 1 as defined above, as catalysts for carrying out (co)polymerization, i.e. polymerization or copolymerization. While carrying out (co)polymerization, the compounds according to the invention also play the role of chain initiator or regulator.

The compounds of formula 1 are particularly useful for carrying out the polymerization of heterocycles. The heterocycles can contain one or more heteroatoms of groups 15 and/or 16, and are of a size ranging from three to eight members. As an example of heterocycles corresponding to the previous formulation, epoxides, thioepoxides, cyclic esters or thioesters such as lactones, lactames and anhydrides can be mentioned.

The compounds of formula 1 are also particularly useful also for carrying out the (co)polymerization of cyclic esters. As an example of cyclic esters, dimer cyclic esters of lactic and/or glycolic acid (lactide and glycolide) can be mentioned. Random or block copolymers can be obtained depending whether monomers are introduced together at the start of the reaction, or sequentially during the reaction.

A subject of the invention is also a process for the preparation of random or block copolymers, or polymers which consist of bringing into contact one or more monomers, a chain initiator, a polymerization catalyst and optionally a polymerization solvent, said process characterized in that the chain initiator and the polymerization catalyst are represented by the same compound which is chosen from the compounds of formula (1) as defined above.

The (co)polymerization can be carried out either in solution or in supercooling. When (co)polymerization is carried out in solution, the reaction solvent can be the (or one of the) substrate(s) used in the catalytic reaction. Solvents which do not interfere with the catalytic reaction itself, are also suitable. As example of such solvents, saturated or aromatic hydrocarbons, ethers, aliphatic or aromatic halides can be mentioned.

The reactions are carried out at temperatures comprised between ambient temperature and approximately 250° C.; the temperature range comprised between 40 and 200° C. proves most advantageous. The durations of the reactions are comprised between 1 and 300 hours, and preferably between 1 and 72 hours.

This (co)polymerization process is particularly suitable for obtaining (co)polymers of cyclic esters, in particular the dimer cyclic esters of lactic and/or glycolic acid. The products obtained such as the biodegradable, lactic glycolic copolymer, are advantageously used as a support in sustained release therapeutic compositions. The process is also particularly suitable for the polymerization of epoxides, in particular propylene oxide. The polymers obtained are compounds which can be used for the synthesis of organic liquid crystals or also as semi-permeable membranes.

The invention also relates to polymers or copolymers which can be obtained by the implementation of a process as described above. The polydispersity (Mw/Mn) of (co) polymers thus obtained can be modified by leaving the reaction mixture at the reaction temperature after the conversion of the monomer(s) is complete. The masses of the (co)polymers are little affected during this process. These phenomena are due to inter- or intra-molecular transesterification reactions (Kiecheldorf et al., Macromolecules, (1988) 21, 286).

The following examples are presented to illustrate the above procedures and should in no way be considered as limiting the scope of the invention.

EXAMPLE 1

[(Me₂CHNCH₂CH₂)₂NMe]Sn

M=Sn; A=B=—CH₂CH₂—; $L_1=L_2$=NCHMe₂; $L_3$=NMe 1.00 g (4.7 mmol) of [(Me₂CHNCH₂CH₂)₂NMe]²⁻, 2Li⁺ and 20 ml of diethylether are introduced successively into a Schlenk tube equipped with a magnetic stirrer and purged under argon. The reaction mixture is cooled down to −78° C., then a suspension of 0.89 g (4.7 mmol) of SnCl₂ in diethylether is introduced. The reaction mixture is taken to ambient temperature then left under agitation for 18 hours at ambient temperature. The solution is filtered and the solvent is evaporated off. The desired compound is isolated in the form of a yellow oil (yield 74%). This compound is characterized by carbon, proton and tin NMR spectroscopy.

NMR $^1$H (C$_6$D$_6$; 250 MHz): 1.49 (d, J$_{HH}$=6.2 Hz, 6H, CHC$\underline{H}_3$); 1.54 (d, J$_{HH}$=6.2 Hz, 6H, CHC$\underline{H}_3$); 2.11 (s, 3H, J119$_{SnC}$=20.2 Hz, J117$_{SnC}$=17.5 Hz, NC$\underline{H}_3$); 2.37 (m, 4H, C$\underline{H}_2$); 3.11 (m, 2H, C$\underline{H}_2$); 3.67 (seven, J$_{HH}$=6.2 Hz, 2H, C$\underline{H}$CH$_3$); NMR $^{13}$C (C$_6$D$_6$; 62.896 MHz): 26.64 (s, CH$\underline{C}H_3$); 26.93 (s, CH$\underline{C}H_3$); 49.05 (s, J$_{SnC}$=53.5 Hz, NCH$_3$); 54.64 (s, CH$_2$); 55.04 (s, $\underline{C}$HCH$_3$); 63.32 (s, $\underline{C}H_2$). NMR $^{119}$Sn (C$_6$D$_6$; 32.248 MHz): 121.13 (V$_{1/2}$=600 Hz).

EXAMPLE 2

[(Me$_3$SiNCH$_2$CH$_2$)$_2$NMe]Sn

M=Sn; A=B=—CH$_2$CH$_2$—; L$_1$=L$_2$=NSiMe$_3$; L$_3$=NMe 1.22 g (4.7 mmol) of [(Me$_3$SiNCH$_2$CH$_2$)$_2$NMe]$^{2-}$, 2Li$^+$ and 20 ml of diethylether are introduced successively into a Schlenk tube equipped with a magnetic stirrer and purged under argon. The reaction mixture is cooled down to −78° C., then a suspension of 0.89 g (4.7 mmol) of SnCl$_2$ in diethylether is introduced. The reaction mixture is taken to ambient temperature then left under agitation for 2 hours at ambient temperature. The solution is filtered, the solvent is evaporated off and the residue is treated with pentane. After evaporation of the solvent, an orange oil is obtained. The desired compound is isolated in the form of white crystals by crystallization from toluene (5 ml) at −20° C. (yield 80%). This compound is characterized by multinuclear magnetic resonance spectroscopy and X-ray diffraction (FIG. 1 and Table 1 below). Melting point 20° C.

EXAMPLE 3

[(Me$_3$SiNCH$_2$CH$_2$)$_2$NMe]Zn (in dimer form)

Figure 2:
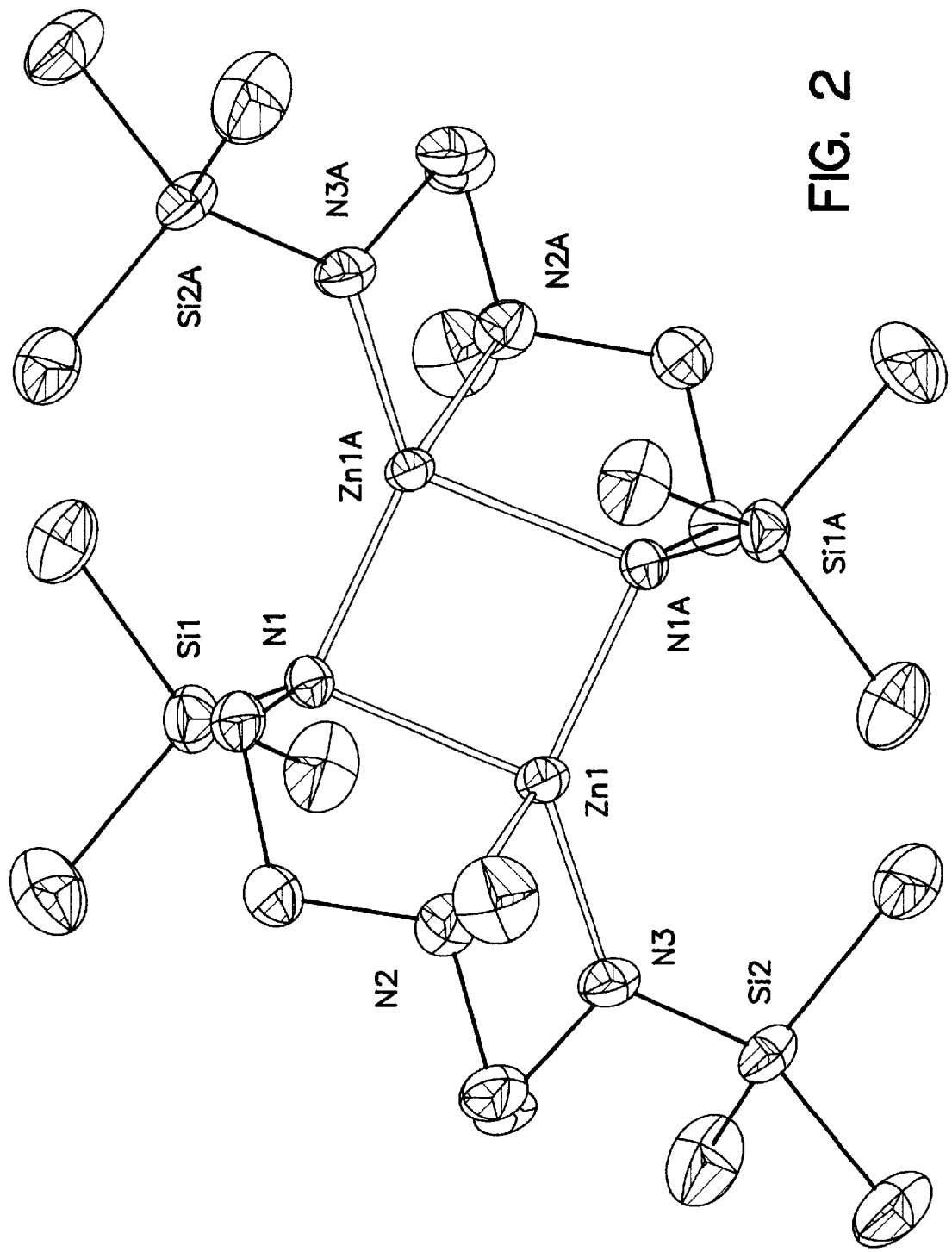

M=Zn; A=B=—CH$_2$CH$_2$—; L$_1$=L$_2$=NSiMe$_3$; L$_3$=NMe 1.1 g (4.2 mmol) of (Me$_3$SiNHCH$_2$CH$_2$)$_2$NMe and 20 mit of toluene are introduced successively into a Schlenk tube equipped with a magnetic stirrer and purged under argon. The reaction mixture is cooled down to −78° C., then 2.1 ml of ZnMe$_2$ (2 M, 4.2 mmole) is introduced. The reaction mixture is taken to ambient temperature then left under agitation for 3 hours. The solvent is then evaporated off. A dark yellow oil is obtained. This oil is heated again at 110° C. for 4 hours. The desired compound is washed with 5 ml of pentane (3 times) and isolated in the form of white crystals (yield 75%). This compound is characterized by NMR spectroscopy and X-ray diffraction (FIG. 2 and Table 2 below).

NMR $^1$H (C$_6$D$_6$; 250 MHz): 0.25 (s, 18H, Si(C$\underline{H}_3$)$_3$); 0.30 (s, 18H, Si(C$\underline{H}_3$)$_3$); 2.11 (s, 6H, NC$\underline{H}_3$); 2.24 (m, 8H, C$\underline{H}_2$); 3.05 (m, 8H, C$\underline{H}_2$). NMR $^{13}$C (C$_6$D$_6$; 50.323 MHz): 3.22 (s, Si($\underline{C}H_3$)$_3$); 3.28 (s, Si($\underline{C}H_3$)$_3$); 44.49 (s, N$\underline{C}H_3$); 47.66 (s, $\underline{C}H_2$); 47.72 (s, $\underline{C}H_2$); 60.31 (s, $\underline{C}H_2$); 65.91 (s, $\underline{C}H_2$).

EXAMPLE 4

Preparation of a Poly(D,L-lactide)

0.08 g (0.21 mmol) of [(Me$_3$SiNCH$_2$CH$_2$)$_2$NMe]Sn, 6.67 g (46.3 mmol) of D,L-lactide and 70 ml of toluene are introduced successively into a Schlenk tube equipped with a magnetic stirrer and purged under argon. The reaction mixture is left under agitation at 75° C. for 2.5 hours. The polymer is characterized by carbon and proton NMR; the conversion of the monomer is 60%. According to an analysis by GPC (Gel Permeation Chromatography) using a calibration carried out from polystyrene (PS) standards of masses 761 to 400000, the sample is composed of polymers having contiguous masses (Mw/Mn=1.43) and high masses (Mw=62500).

EXAMPLE 5

Preparation of a Poly(D,L-lactide)

0.02 g (0.062 mmol) of [(Me$_3$SiNCH$_2$CH$_2$)$_2$NMe]Zn, 0.621 g (43.1 mmol) of D,L-lactide and 50 ml of toluene are introduced successively into a Schlenk tube equipped with a magnetic stirrer and purged under argon. The reaction mixture is left under agitation at 30° C. for 36 hours. The polymer is characterized by carbon and proton NMR; the conversion of the monomer is 92%. According to an analysis by GPC (Gel Permeation Chromatography) using a calibration carried out from polystyrene (PS) standards of masses 761 to 400000, the sample is composed of polymers having high masses (Mw=34654).

EXAMPLE 6

Preparation of a Block (D,L-lactide/glycolide) Copolymer 0.08 g (0.21 mmol) of [(Me$_3$SiNCH$_2$CH$_2$)$_2$NMe]Sn, 5.00 g (34.72 mmol) of D,L-lactide and 70 ml of toluene are introduced successively into a Schlenk tube equipped with a magnetic stirrer and purged under argon. The reaction mixture is left under agitation at 75° C. for 4 hours. Proton NMR analysis allows verification that conversion of the monomer is greater than 95%. 1.00 g (8.6 mmol) of glycolide is added to the preceding solution. The reaction mixture is left under agitation at 75° C. for 1 hour. Proton NMR analysis of an aliquot shows that a copolymer is formed. The ratio of the signal integrals corresponding to the polylactide part (5.20 ppm) and the polyglycolide part (4.85 ppm) is 8/1. According to a GPC analysis, using a calibration carried out from PS standards of masses 761 to 400000, this copolymer is a mixture of macromolecules (Mw/Mn=2.35) of high masses (Mw=68950).

EXAMPLE 7

Modification of the Polydispersity of a (D,L-lactide/glycolide) Copolymer

A copolymer prepared according to Example 4 (Mw/Mn=2.35) is left at 75° C. for 20 hours. GPC analysis of an aliquot shows that the dispersity has increased and that the mass remains constant (Mw/Mn=2.69; Mw=68850). The mixture is again left for 20 hours at 75° C. GPC analysis of an aliquot shows that the dispersity starts to decrease and that the mass remains roughly constant (Mw/Mn=2.02; Mw=65659). After heating for another 40 hours at 75° C., the polydispersity is 1.53 for masses of 62906.

EXAMPLE 8

Preparation of a Random (D,L-lactide/glycolide) Copolymer 0.08 g (0.21 mmol) of [(Me$_3$SiNCH$_2$CH$_2$)$_2$NMe]Sn, 4.70 g (32.63 mmol) of D,L-lactide and 1.00 g (8.61 mmol) of glycolide are introduced successively into a Schlenk tube equipped with a magnetic stirrer and purged under argon. The reaction mixture is heated at 178° C. for 1.2 hours. The polymer is characterized by carbon and proton NMR; the conversion of the monomers is total. According to a GPC analysis, using a calibration carried out from PS standards of masses 761 to 400000, the sample is composed of polymers having a polydispersity (Mw/Mn) of 2.24 and masses (Mw) of 21650.

EXAMPLE 9

Preparation of a Random (D,L-lactide/glycolide) Copolymer having a Lactide/Glycolide Composition Close to 50/50

0.01 g (0.031 mmol) of $[(Me_3SiNCH_2CH_2)_2NMe]Zn$, 5.55 g (38.5 mmol) of D,L-lactide and 1.91g (16.5 mmol) of glycolide are introduced successively into a Schlenk tube equipped with a magnetic stirrer and purged under argon. The reaction mixture is left under agitation at 180° C. for 144 minutes. Proton NMR analysis allows verification that conversion of the monomers is 76% of lactide and 100% of glycolide. The ratio of the signal integrals corresponding to the polylactide part (5.20 ppm) and the polyglycolide part (4.85 ppm) allows the composition of the copolymer to be evaluated at 46/54. According to GPC analysis, using a calibration carried out from PS standards of masses 761 to 400000, this copolymer is a mixture of macromolecules (Mw/Mn=1.82) of high masses (Mw=36192).

EXAMPLE 10

Preparation of a Random (D,L-lactide/glycolide) Copolymer of High Masses having a Lactide/Glycolide Composition Close to 70/30

0.015 g (0.046 mmol) of $[(Me_3SiNCH_2CH_2)_2NMe]Zn$, 13.3 g (92.4 mmol) of D,L-lactide and 3.1g (26.4 mmol) of glycolide are introduced successively into a Schlenk tube equipped with a magnetic stirrer and purged under argon. The reaction mixture is left under agitation at 180° C. for 5 hours. Proton NMR analysis allows verification that the conversion of the monomers is 68% of lactide and 100% of glycolide. The ratio of the signal integrals corresponding to the polylactide part (5.20 ppm) and the polyglycolide part (4.85 ppm) allows the composition of the copolymer to be evaluated at 68% of lactide and 32% of glycolide. According to a GPC analysis, using a calibration carried out from PS standards of masses 761 to 400000, this copolymer is a mixture of macromolecules (Mw/Mn 2.30) of high masses (Mw=71281).

TABLE 1 length of selected bonds (in Angström) and bond angles (in degrees) for the compound of Example 2.

| Sn(1)-N(1) | 2.117 (6) Å | C(4)-C(5) | 1.497 (11) Å |
|---|---|---|---|
| Sn(1)-N(2) | 2.323 (6) Å | C(5)-N(2) | 1.485 (10) Å |
| Sn(1)-N(3) | 2.082 (5) Å | N(2)-C(6) | 1.483 (10) Å |
| N(1)-Si(1) | 1.712 (6) Å | N(2)-C(7) | 1.488 (9) Å |
| N(3)-Si(2) | 1.706 (13) Å | C(7)-C(8) | 1.528 (11) Å |
| N(1)-C(4) | 1.458 (9) Å | C(8)-N(3) | 1.426 (9) Å |
| N(1)-Sn(1)-N(2) | 77.4 (2)° | N(2)-Sn(1)-N(3) | 79.0 (2)° |
| Sn(1)-N(1)-C(4) | 116.7 (4)° | Sn(1)-N(3)-C(8) | 109.4 (4)° |
| N(3)-Sn(1)-N(1) | 98.1 (2)° | | |

TABLE 2 length of selected bonds (in Angström) and bond angles (in degrees) for the compound of Example 3.

| Zn(1)-N(1) | 2.105 (2) | C(4)-C(5) | 1.523 (3) |
|---|---|---|---|
| Zn(1)-N(2) | 2.239 (2) | C(5)-N(2) | 1.479 (3) |
| Zn(1)-N(3) | 1.907 (2) | N(2)-C(6) | 1.473 (3) |
| Zn(1)-N(1)A | 2.025 (2) | N(2)-C(7) | 1.484 (3) |
| Si(1)-N(1) | 1.736 (2) | C(8)-N(3) | 1.465 (3) |
| N(3)-Si(2) | 1.694 (2) | C(7)-C(8) | 1.514 (3) |
| N(1)-C(4) | 1.492 (2) | N(1)-Zn(1)-N(1)A | 92.49 (6) |
| N(1)-Zn(1)-N(2) | 85.25 (6) | N(3)-Zn(1)-N(2) | 86.96 (7) |
| C(4)-N(1)-Zn(1) | 103.84 (11) | C(8)-N(3)-Zn(1) | 106.13 (12) |
| N(3)-Zn(1)-N(1) | 124.48 (7) | Zn(1)-N(1)-Zn(1)A | 87.51 (6) |

What is claimed is:

1. A compound of the formula

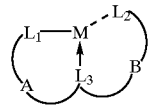

(1)

wherein M is an element selected from the group consisting of tin zinc, cadmium, mercury, germanium and lead, A and B are individually alkylene of 2 to 4 carbon atoms unsubstituted or substituted by a member of the group consisting of alkyl of 1 to 6 carbon atoms, cycloalkyl of 3 to 7 carbon atoms and aryl which members may be optionally substituted with at least one member of the group consisting of halogen, $-NO_2$, $-CN$ and alkyl of 1 to 6 carbon atoms, $L_1$, $L_2$ and $L_3$ are individually $-E_{15}(R_{15})$, $E_{15}$ is an element of group 15 of the Periodic Table and $R_{15}$ is selected from the group consisting of a) -hydrogen, b) cycloalkyl of 3 to 7 carbon atoms and aryl, both unsubstituted or substituted with at least one member of the group consisting of halogen, $-NO_2$, $-CN$ and alkyl of 1 to 6 carbon atoms, c) $RR'R''E_{14}-$, $E_{14}-$ is an element of group 14 of the Periodic Table, R, R' and R" are individually selected from the group consisting of hydrogen, and alkyl of 1 to 6 carbon atoms, cycloalkyl of 3 to 7 carbon atoms, aryl, alkoxy of 1 to 6 carbon atoms, cycloalkoxy of 3 to 7 carbon atoms, aryloxy, alkylthio of 1 to 6 carbon atoms, cycloalkylthio of 3 to 7 carbon atoms, and arylthio, all unsubstituted or substituted with at least one member of group consisting of halogen, $-NO_2$, $-CN$ and alkyl of 1 to 6 carbon atoms, and d) $-SO_2R'_{15}$ and $R'_{15}$ is selected from the group consisting of a) halogen, b) alkyl of 1 to 6 carbon atoms and haloalkyl of 1 to 6 carbon atoms, atoms, c) aryl optionally substituted with at least one member of the group consisting of alkyl of 1 to 6 carbon atoms, haloalkyl of 1 to 6 carbon atoms and halogen.

2. A compound of claim 1 wherein M is zinc or tin, A and B are individually alkylene of 2 to 4 carbon atoms, $L_1$, $L_2$ and $L_3$ are individually $-E_{15}(R_{15})$, $E_{15}$ is nitrogen or phosphorous, $R_{15}$ is $RR'R''E_{14}-$, $E_{14}$ is carbon or silicon and R, R' and R" are individually selected from the group consisting of hydrogen, alkyl of 1 to 6 carbon atoms and aryl.

3. A compound of claim 2 wherein A and B are ethylene and R, R' and R" are individually hydrogen or alkyl of 1 to 6 carbon atoms.

4. A compound of claim 1 wherein M is tin or zinc, A and B are ethylene, $L_1$, $L_2$ and $L_3$ are individually $-E_{15}(R_{15})$, $E_{15}$ is nitrogen, $R_{15}$ is $RR'R''-E_{14}-$, $E_{14}$ is carbon or silicon and R,R' and R" are individually selected from the group consisting of hydrogen, methyl, ethyl, propyl and isopropyl.

5. The compound of general formula I as defined in claim 1 and corresponding to the following formulae:

—[(Me$_2$CHNCH$_2$CH$_2$)$_2$NMe]Sn;

—[(Me$_3$SiNCH$_2$CH$_2$)$_2$NMe]Sn;

—[(Me$_3$SiNCH$_2$CH$_2$)$_2$NMe]Zn.

6. Process for the preparation of the products of general formula I as defined in claim 1, characterized in that a product of formula I $$(L_1\text{—}A\text{—}L_3\text{—}B\text{—}L_2)^{2-}, 2Y^+ \qquad \text{I}$$

in which $L_1$, A, $L_3$, B and $L_2$ have the meanings indicated in claim 1 and Y represents an organometallic group, a metal or hydrogen atom, is reacted with a product of formula II $$MZ_1Z_2 \qquad \text{(II)}$$

in which M has the meaning indicated in claim 1 and $Z_1$ and $Z_2$ represent, independently, a parting group, in order to obtain a product of formula I.

7. In a process for the preparation of block and random copolymers or polymers comprising reacting at least one monomer with a polymerization catalyst and optionally a polymerization solvent at room temperature up to 250° C. for 1 to 300 hours, the improvement comprising using a compound of claim 1 as the polymerization catalyst.

8. The process of claim 7 wherein the monomer is an epoxide or a cyclic ester.

9. The process of claim 7 wherein the monomer is selected from the group consisting of propylene oxide and dimeric cyclic esters of lactic acid and/or glycolic acid.

10. A polymer or copolymer produced by the process of claim 7.

11. In a process for the polymerization of dimeric cyclic esters of lactic acid and/or glycolic acid, the improvement comprising using a polymerization catalyst of claim 1.

12. In the polymerization of a heterocycle epoxide, the improvement comprising using as the polymerization catalyst the catalyst of claim 1.

13. The method of claim 12 wherein the epoxide is propylene oxide.

* * * * *